United States Patent [19]

Goosen et al.

[11] Patent Number: 4,792,335
[45] Date of Patent: Dec. 20, 1988

[54] PRESSURE CONTROLLED VALVE APPARATUS

[76] Inventors: Carl C. Goosen; Bernard T. Goosen, both of 2415 Shoreham Rd., Orlando, Fla. 32803

[21] Appl. No.: 13,375

[22] Filed: Feb. 11, 1987

[51] Int. Cl.$^4$ .............................................. A61M 1/00
[52] U.S. Cl. ..................................... 604/323; 128/762
[58] Field of Search .............. 604/317, 323, 335, 350; 128/760, 762, 766, 767; 137/469, 540

[56] References Cited

U.S. PATENT DOCUMENTS

| | | | |
|---|---|---|---|
| 2,431,769 | 12/1947 | Parker | 137/469 |
| 3,626,980 | 12/1971 | Svensson | 604/323 |
| 4,265,118 | 5/1981 | Griesel | 128/767 |
| 4,559,049 | 12/1985 | Haan | 604/323 |

Primary Examiner—Stephen C. Pellegrino
Assistant Examiner—J. L. Kruter
Attorney, Agent, or Firm—A. W. Fisher, III

[57] ABSTRACT

A pressure controlled valve apparatus for use with a catheterized bladder or the like to selectively control fluid flow therefrom comprising a fluid reservoir including a primary fluid reservoir chamber and a secondary fluid reservoir chamber in open fluid communication relative to each other to receive fluid from the catheterized bladder and a fluid flow control including a primary control valve and a secondary control valve each selectively movable between a first and second position, the primary control valve disposed to seal the primary fluid reservoir chamber when in the first position and to unseal the primary fluid reservoir chamber when in the second position in response to a first predetermined pressure to release fluid from the catheterized bladder and the primary fluid reservoir chamber to a fluid collection container and the secondary control valve disposed to seal the secondary fluid reservoir chamber when in the first position and to unseal the secondary fluid reservoir chamber when in the second position in response to a second predetermined pressure to release fluid from the catheterized bladder and the secondary fluid reservoir chamber to a fluid collection container.

30 Claims, 1 Drawing Sheet

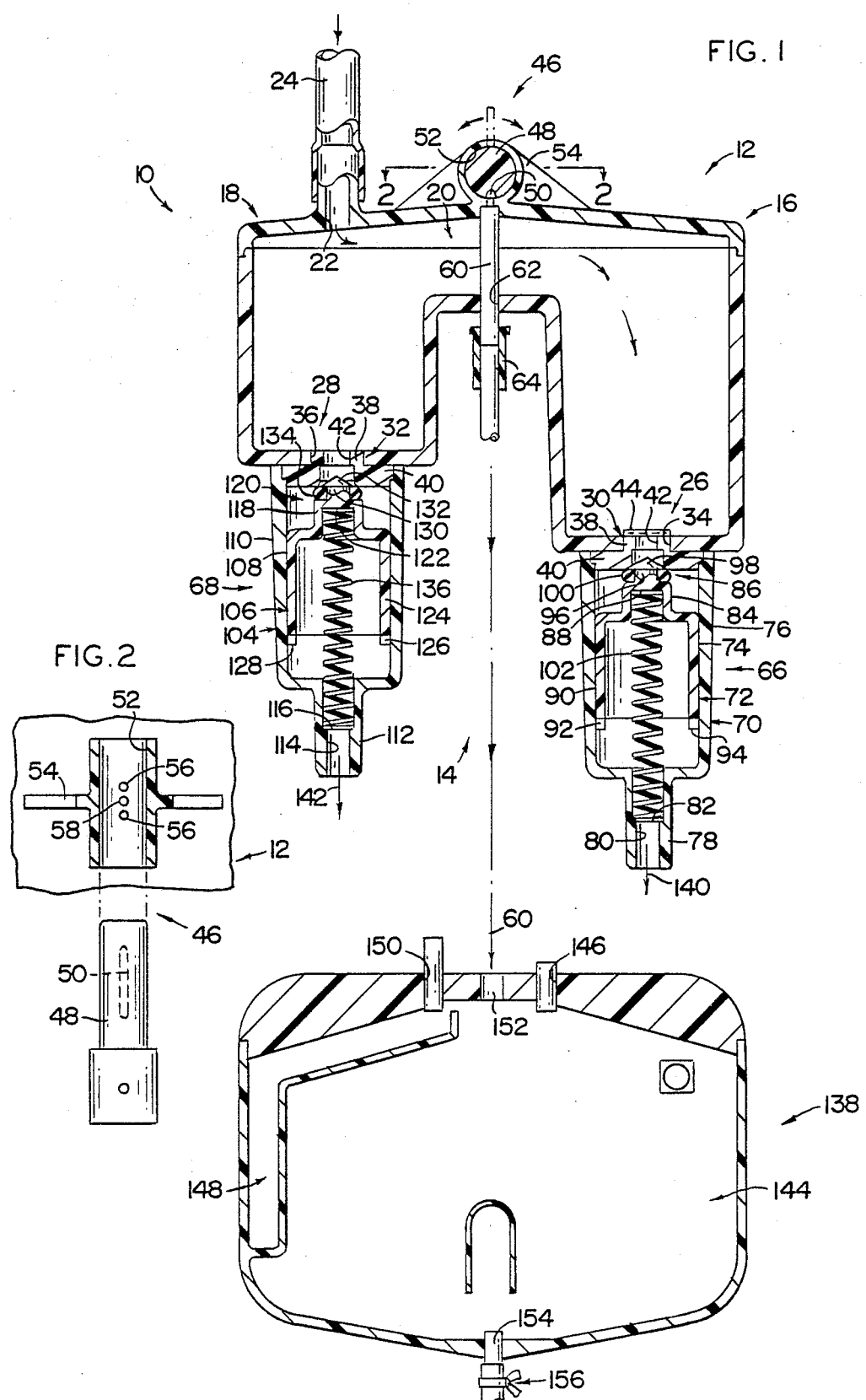

PRESSURE CONTROLLED VALVE APPARATUS

BACKGROUND OF THE INVENTION

1. Field of the Invention

A pressure controlled valve apparatus for use with a catheterized bladder of the like to selectively control fluid flow therefrom at a predetermined pressure.

2. Description of the Prior Art

Various efforts have been made to control the bladder volume of patients undergoing bladder catheterization. A common procedure to obtain continuous drainage of urine from the urinary bladder employs a catheter passed transurethrally and retained in the bladder by standard and conventional devices. Generally such continuous drainage is without periodic filling and emptying of the bladder.

Unfortunately such procedures or techniques exhibit several significant shortcomings. The urinary bladder is a hollow distensible organ requiring alternate filling and emptying to maintain the tone of the muscular walls. Such periodic filling and emptying of the bladder is one of the major mechanisms by which the concentration of bacteria in the bladder is kept at biologically acceptable levels. This mechanism dilutes the bacteria present in the bladder with sterile urine from the ureters with periodic and complete emptying of the bladder. If the bladder is kept from emptying completely, although still allowed to partially expel the contents periodically or continually, the growth of bacteria in the bladder may be of such magnitude that infection will result.

Moreover such indwelling bladder catheters generally do not conform to the contracted shape of the bladder so that "foley tip necrosis" of the dome of the bladder may result. Such a pressure ischemic ulcer of the dome may be the portal by which bacteria enter to infect the bladder. Such infections, common in patients with indwelling catheters, are caused when the dome of the bladder collapses or is drawn down over the indwelling catheter.

Numerous attempts have been made to improve such drainage systems. U.S. Pat. Nos. 2,602,448 and 2,860,636 show drainage and irrigating units utilizes a siphon in combination with a reservoir to provide cycle draining of the bladder. However, these systems like other siphon systems, require a loop be fed at a predetermined height above the patient's bladder to create two siphon legs which will create the pressure at which the siphon will empty the bladder. Pressure release is controlled by raising the height of the device on a bedside support and is very precise and subject to variations by a shifting patient and preventing patient from moving around while the catheter is in place.

U.S. Pat. No. 3,598,124 discloses a siphon leg controlled by attaching the catheter to a support at predetermined adjusted height to vary the pressure at which the bladder will drain with a flutter valve near the patient to break the siphon action of the system once the bladder has drained.

U.S. Pat. No. 4,230,102 discloses a device for the draining of a urine bladder using a T-joint placed on a catheter with a pressure membrane attached thereto in a large casing for actuating a pressure switch which in turn actuates an electric motor driving a gear train and cam. A cam follower is spring loaded to clamp the catheter for two minute cycles upon actuation by the pressure switch to drain the bladder.

U.S. Pat. No. 3,768,102, shows an implantable artificial urethal valve, while U.S. Pat. No. 3,642,004 discloses a urethal valve employing an electrically actuated solenoid. U.S. Pat. No. 3,419,009 discloses a vented surgical drainage tube for bladder irrigation utilizing an electrical control system with a timing cam.

U.S. Pat. No. 4,424,058 shows a drainage control valve apparatus that utilizes a pressure relief valve opening upon a predetermined fluid pressure and a liquid column to hold the pressure relief valve open under the weight of the liquid column escaping past the pressure relief valve to apply a negative pressure to the back of a pressure relief valve element.

SUMMARY OF THE INVENTION

The present invention relates to a pressure controlled apparatus comprising a fluid reservoir and fluid flow control for use with a catheterized bladder or the like to selectively control fluid flow therefrom.

The fluid reservoir comprises a primary and secondary fluid reservoir chamber coupled in open fluid communication through a fluid flow channel. The fluid reservoir includes an inlet port in open fluid communication with the catheterized bladder through an inlet conduit in combination with a primary and secondary outlet formed in the lower portions of the primary and secondary reservoir chambers respectively. A filter is disposed adjacent the primary outlet to prevent debris from fluid passing therethrough.

The fluid flow control comprises a primary and secondary control valve to selectively seal the primary and secondary fluid reservoir chambers respectively.

The primary and secondary control valve each comprises an outer hollow element and an inner hollow valve element movably disposed in spaced relationship thereto to cooperatively form a fluid flow feed channel therebetween. Each outer hollow valve element includes a primary outlet port and lower valve bias seat. Each inner hollow valve element includes a seal and upper valve bias seat formed in the upper portion thereof and lower enlarged member having at least one fluid flow aperture formed on the lower portion thereof. A valve bias is retained between the upper and lower valve bias seats normally biasing the inner hollow valve element in the first or closed position to seal the outlet ports of the primary and secondary control valves.

Each outlet port is coupled in open fluid communication with a fluid collector container.

In use, the primary control valve opens when a first predetermined pressure of the bladder is reached. Opening of the primary control valve is achieved when the bladder pressure is balanced with the valve pressure and a small spike of additional pressure caused by normal physiological phenomenon opens the primary control valve. Flow through the primary control valve holds the inner hollow valve element in the second or open position by the capillary force or Coanda effect created by fluid flow through the fluid flow feed channel. This force will maintain the flow until the bladder is emptied. This force behaves like a venturi to load the valve bias. When fluid flow ceases, the valve bias forces the inner hollow valve element to the first or closed position to seal the primary outlet port. When the filter has accumulated debris the secondary control valve will open at a second predetermined pressure to operate in a similar manner.

Leakage of the primary and secondary control valves is further prevented by the absence of distal siphoning forces. The capillary force maintains film of liquid in the fluid flow feed channels for more complete sealing. Bladder release pressure may be controlled by varying the pressure head by raising or lowering the pressure controlled apparatus.

Absence of suction mechanisms permits the bladder to maintain a pressure of substantially zero while emptying with no residual negative pressure, simulating the normal biological pressure except for the brief pressure spikes before voiding and momentarily when voiding commences.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is cross-sectional front view of the pressure controlled valve apparatus.

FIG. 2 is a view of the air priming means taken along line 2—2 of FIG. 1.

Similar reference characters refer to similar parts throughout the several views of the drawings.

DETAILED DESCRIPTION OF THE PREFERRED EMBODIMENT

As shown in FIG. 1, the present invention relates to a pressure controlled valve apparatus generally indicated as 10 comprising a fluid reservoir and fluid flow control generally indicated as 12 and 14 respectively for use with a catheterized bladder or the like to selectively control fluid flow therefrom.

The fluid reservoir 12 comprises a primary and secondary fluid reservoir chamber generally indicated as 16 and 18 respectively coupled in open fluid communication through a fluid flow channel 20. The fluid reservoir 12 includes an inlet port 22 in open fluid communication with the catheterized bladder through an inlet conduit 24 in combination with a primary and secondary outlet generally indicated as 26 and 28 respectively formed in the lower portion of the primary and secondary reservoir chambers 16 and 18 respectively. The primary and secondary outlet 26 and 28 include a primary and secondary valve seat generally indicated as 30 and 32 respectively disposed in operatively relationship relative to a primary and secondary aperture 34 and 36 respectively formed in the lower portions of the primary and secondary reservoir chamber 16 and 18 respectively. The primary and secondary valve seats 30 and 32 each include an upper reduced portion 38 and a lower enlarged portion 40 having a centrally disposed fluid outlet channel 42 formed therethrough. The upper reduced portions 38 are press fitted through the primary and secondary apertures 34 and 36 such that the lower enlarged portions 40 engage the lower surfaces of the primary and secondary fluid reservoir chambers 16 and 18. A filter 44 is affixed to the upper reduced portion 38 of the primary valve seat 30 to filter debris from fluid passing through the centrally disposed fluid outlet channel 42.

An air priming means generally indicated as 46 is formed on the upper portion of the fluid reservoir 12. As shown in FIGS. 1 and 2, the air priming means 46 comprises a substantially cylindrical solid sealing member 48 having a flow recess or chamber 50 formed on the surface thereof rotatably disposed within a substantially cylindrical channel 52 formed through a mounting member 54, at least one air inlet aperture and an air outlet aperture indicated as 56 and 58 respectively formed in the upper portion of the fluid reservoir 12 and a flexible air outlet conduit 60 in open fluid communication with the air outlet aperture 58 extending through an aperture 62 formed in the lower portion of the fluid reservoir 12. A stiffener member 64 is coupled to the flexible air outlet conduit 60 adjacent the aperture 62.

The fluid flow control 14 comprises a primary and secondary control valve generally indicated as 66 and 68 respectively to selectively seal the primary and secondary fluid reservoir chambers 16 and 18 respectively.

The primary control valve 66 comprises an outer hollow substantially cylindrical valve element generally indicated 70 having an inner hollow substantially cylindrical valve element generally indicated as 72 movably disposed in spaced relationship thereto to cooperatively form a fluid flow feed channel 74 therebetween. The outer hollow substantially cylindrical valve element 70 comprises an upper enlarged member 76 affixed to the lower enlarged portion 40 of the primary valve seat 30 and a lower reduced member 78 including a primary outlet port 80 formed therethrough having a lower valve bias seat 82 formed therein. The inner hollow substantially cylindrical valve element 72 comprises an upper reduced member 84 including a primary seal generally indicated as 86 formed on the upper portion thereof and an upper valve bias seat 88 formed on the inner portion thereof and a lower enlarged member 90 having at least one fluid flow aperture 92 formed on the lower portion thereof. The fluid flow aperture 92 formed in the lower portion of the lower enlarged member 90 may comprise a plurality of legs each indicated as 94 cooperatively forming the fluid flow apertures 92 therebetween. The primary seal 86 comprises a reduced intermediate portion 96 and upper triangularly shaped alignment cap 98 to cooperatively retain a seal element or O-ring 100. A valve bias 102 is retained by the upper and lower valve bias seats 88 and 82 normally biasing the inner hollow substantially cylindrical valve element 72 in the upper or closed position such that the seal element 100 seals the centrally disposed fluid outlet channel 42 of the primary valve seat 30.

The secondary control valve 68 is similarly constructed. Specifically, the secondary control valve 68 comprises an outer hollow substantially cylindrical vavve element generally indicated as 104 having an inner hollow substantially cylindrical valve element generally indicated as 106 movably disposed in spaced relationship thereto to cooperatively form a fluid flow feed channel 108 therebetween. The outer hollow substantially cylindrical valve element 104 oomprises an upper enlarged member 110 affixed to the lower enlarged portion 40 of the secondary valve seat 32 and a lower reduced member 112 including a secondary outlet port 114 formed therethrough having a lower valve bias seat or shoulder 116 formed therein. The inner hollow substantially cylindrical valve element 106 comprises an upper reduced member 118 including a secondary seal generally indicated as 120 formed on the upper portion thereof and an upper valve bias seat 122 formed on the inner portion thereof and a lower enlarged member 124 having at least one fluid flow aperture 126 formed on the lower portion thereof. The fluid flow aperture 166 formed in the lower portion of the lower enlarged member 124 may comprise a plurality of legs each indicated as 128 cooperatively forming the fluid flow apertures 126 therebetween. The secondary seal 120 comprises a reduced intermediate portion 130 and upper triangularly shaped alignment tip 132 to cooperatively retain a seal element or O-ring 134. A valve bias 136 is retained by the upper and lower valve bias seats 122 and 116 normally biasing the inner hollow substantially cylindrical valve element 106 in the upper or closed position such that the seal element 134 seals the centrally disposed fluid outlet channel 42 of the secondary valve seat 32.

The primary outlet port 80, secondary outlet port 114 and air outlet aperture 58 are operatively coupled to a fluid collector container generally indicated as 138 through a primary fluid outlet conduit 140, secondary fluid outlet conduit 142 and the flexible air outlet conduit 60 respectively. The fluid collector container 138 comprises a primary fluid chamber 144 coupled to the primary fluid outlet conduit 140 through a primary inlet port 146, a visual monitor compartment 148 coupled to the secondary fluid outlet conduit 142 through a secondary inlet port 150 and an air inlet port 152 coupling the primary fluid chamber 144 to the flexible air outlet conduit 60. A fluid outlet 154 and clamp or valve 156 are formed on the lower portion of the primary fluid chamber 44 to permit emptying thereof. When the filter 44 becomes clogged causing flow through the secondary control valve 68, fluid accumulating in the visual monitor compartment 148 indicates the pressure controlled valve aperture 10 must be changed.

In use, the primary control valve 66 opens when a first predetermined pressure of the bladder is reached moving the inner hollow cylindrical channel valve element 72 downward to the second position allowing fluid to flow from the bladder and fluid reservoir 12 through the centrally disposed fluid outlet channel 42, fluid flow feed channel 74, fluid flow aperture 92, primary outlet port 80 and primary fluid outlet conduit 140 to the primary fluid chamber 144. Opening of the primary control valve 66 is achieved when the bladder pressure is balanced with the valve pressure of the primary control valve 66 and a small spike of additional pressure caused by normal physiological phenomenon opens the primary control valve 66. Flow through the primary control valve 66 holds the inner hollow substantially cylindriaal valve element 72 in the second or open position by the capillary force or Coanda created by fluid flow through the fluid flow feed channel 74. This force will maintain the flow until the bladder is emptied. This force behaves as a venturi to load the valve bias 102. When fluid flow ceases, the valve bias 102 forces the inner hollow substantially cylindrical valve element 72 to the first or closed position to seal the primary outlet port 26.

When the filter 44 has accumulated debris the secondary control valve 68 will open at a second predetermined pressure to operate in a similar manner. Specifically, the secondary control valve 68 opens when a second predetermined pressure of the bladder is reached moving the inner hollow substantially cylindrical valve element 106 downward to the second position allowing fluid to flow from the bladder and fluid reservoir 12 through the centrally disposed fluid outlet channel 42, fluid flow feed channel 108, fluid flow aperture 126, secondary outlet port 114 and secondary outlet conduit 142 to the visual monitor compartment 148. Opening of the secondary control valve 68 is achieved when the bladder pressure is balanced with the valve pressure of the secondary control valve 68 and a small spike of additional pressure caused by normal physiological phenomenon opens the secondary control valve 68. Flow through the secondary control valve 68 holds the inner hollow substantially cylindrical valve element 106 in the second or open position by the capillary force or Coanda created by fluid flow through the fluid flow feed channel 108. This force will maintain the flow until the bladder is emptied. This force behaves as a venturi to load the valve bias 134. When fluid flow ceases, the valve bias 134 forces the inner hollow substantially cylindrical valve element 106 to the first or closed position to seal the secondary outlet port 28.

Air priming is accomplished by rotating the sealing member 48 aligning the flow recess 50 in registry with the air inlet aperture 56 and air outlet aperture 58 to feed air from the fluid reservoir 12 through air inlet aperture 56, flow recess 50 and out air outlet aperture 58 to and the air outlet conduit valve 60.

Leakage of the primary and secondary control valves 66 add 68 is further prevented by the absence of distal siphoning forces. The capillary force maintains a film of liquid in the fluid flow feed channels 74 and 108 for more complete sealing.

The bladder release pressure may be controlled by varying the pressure head by raising or lowering the pressure controlled valve apparatus 10.

Absence of suction mechanisms permits the bladder to maintain a pressure of substantially zero while emptying with no residual negative pressure, simulating the normal biological pressure except for the brief pressure spikes before voiding and momentarily when voiding commences.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described and all statements of the scope of the invention which, as a matter of language, might be said to fall therebetween;

Now that the invention has abeen described, what is claimed is:

1. A pressure controlled valve apparatus for use with a catheter to selectively control fluid flow therefrom comprising a fluid reservoir coupled to the catheter through an inlet port including a primary fluid reservoir chamber to receive fluid from the catheter having a primary outlet formed in the lower portion thereof and a fluid flow control including a primary control valve selectively movable between a first and second position, said primary control valve disposed to seal said primary outlet when in said first position and to unseal said primary outlet when in said second position in response to a first predetermined pressure to release fluid from the catheter and said primary fluid reservoir chamber, said primary control valve comprises an outer hollow substantially cylindrical valve element including a lower valve bias seat formed therein and an inner hollow substantially cylindrical valve element including an upper valve bias seat formed therein, said inner hollow substantially cylindrical valve element movable between a first and second position disposed in spaced relationship relative to said outer hollow valve element to cooperatively form a substantially cylindrical fluid flow feed channel therebetween such that fluid flow through said substantially cylindrical fluid flow feed channel maintains said inner hlllow substantially cylindrical valve element in said second position until said primary fluid reservoir chamber is empty, and a bias means operative disposed in said lower valve bias seat and said upper valve bias seat to normally maintain said inner hollow valve element in said first position, flow through said primary control valve holds said inner valve element in the second position by capillary force created by fluid flow through said fluid flow channel and thereafter when fluid from the primary valve ceases to occur.

2. The pressure control valve apparatus of claim 1 wherein said primary outlet comprises a primary valve seat disposed in operative relationship to a primary aperture formed in the lower portion of said primary fluid reservoir chamber.

3. The pressure control valve apparatus of claim 2 wherein said primary valve seat comprises an upper reduced portion at least partially disposed within said primary aperture and a lower enlarged portion having a centrally disposed fluid outlet channel formed therethrough in open fluid communication with the interior of said primary fluid reservoir chamber.

4. The pressure control valve apparatus of claim 3 wherein said outer hollow substantially cylindrical valve element comprises an upper enlarged member affixed to said lower enlarged portion of said primary valve seat and a lower reduced portion including a primary outlet port formed therethrough having said lower valve bias seat formed therein.

5. The pressure control valve apparatus of claim 4 wherein said inner hollow substantially cylindrical valve element comprises an upper reduced member including a primary seal formed on the upper portion thereof and said upper valve bias seat formed on the inner portion thereof and a lower enlarged member having at least one fluid flow aperture formed on the lower portion thereof.

6. The pressure control valve apparatus of claim 5 wherein said primary seal comprises a reduced intermediate portion and upper alignment portion to cooperatively retain a seal element thereon, said valve bias being retained by said upper and lower valve bias seats normally biasing said inner hollow valve element in said first position such that said seal element seals said centrally disposed fluid outlet channel.

7. The pressure controlled valve apparatus of claim 6 wherein said fluid reservoir further includes a secondary fluid reservoir chamber to receive fluid from the catheterized bladder having a secondary outlet formed in the lower portion thereof and said fluid flow control further includes a secondary control valve selectively movable between a first and second position, said secondary control valve disposed to seal said secondary outlet when in said first position and to unseal said secondary outlet when in said second position in response to a second predetermined pressure to release fluid from the catheterized bladder and said secondary fluid reservoir chamber.

8. The pressure controlled valve apparatus of claim 7 wherein said secondary fluid reservoir chamber is in open fluid communication with said primary fluid reservoir chamber through a fluid flow channel to feed fluid from the catheterized bladder through said inlet port, said secondary fluid reservoir chamber and said fluid flow channel to said primary fluid reservoir chamber.

9. A pressure controlled valve apparatus of claim 6 wherein said secondary control valve comprises an outer hollow substantially cylindrical valve element including a lower valve bias seat formed therein and an inner hollow substantially cylindrical valve element including an upper valve bias seat formed therein, said inner hollow substantially cylindrical valve element movable between a first and second position disposed in spaced relationship relative to said outer hollow valve element to cooperatively form a substantially cylindrical fluid flow feed channel therebetween such that fluid flow through said substantially cylindrical fluid flow feed channel maintains said inner hollow substantially cylindrical valve element in said second position until said secondary fluid reservoir chamber is empty, and a bias means operative disposed in said lower valve bias seat and said upper valve bias seat to normally maintain said inner hollow valve element in said first position.

10. The pressure control valve apparatus of claim 9 wherein said secondary outlet comprises a secondary valve seat disposed in operative relationship to a secondary aperture formed in the lower portion of said secondary fluid reservoir chamber.

11. The pressure control valve apparatus of claim 10 wherein said secondary valve seat comprises an upper reduced portion at least partially disposed within said secondary aperture and a lower enlarged portion having a centrally disposed fluid outlet channel in open fluid communication with the interior of said secondary fluid reservoir chamber.

12. The pressure control valve apparatus of claim 11 wherein said outer hollow valve element comprises an upper enlarged member affixed to said lower enlarged portion of said second valve seat and a lower reduced portion including a secondary outlet port formed therethrough having said lower valve bias seat formed therein.

13. The pressure control valve apparatus of claim 12 wherein said inner hollow valve element comprises an upper reduced member including a secondary seal formed on the upper portion thereof and said upper valve bias seat formed on the inner portion thereof and a lower enlarged member having at least one fluid flow aperture formed on the lower portion thereof.

14. The pressure control valve apparatus of claim 13 wherein said secondary seal comprises a reduced intermediate portion and upper alignment portion to cooperatively retain a seal element thereon, said valve bias being retained by said upper and lower valve bias seats normally biasing said inner hollow valve element in said first position such that said seal element seals said centrally disposed fluid outlet channel.

15. The pressure controlled valve apparatus of claim 14 further comprises a fluid collector container including a primary fluid chamber having a primary inlet formed therein coupled to said primary outlet port of said primary fluid reservoir chamber through a primary fluid outlet conduit to selectively receive fluid from said primary fluid reservoir chamber.

16. The pressure controlled valve apparatus of claim 15 wherein said fluid collector container further includes a visual monitor compartment having a secondary inlet port formed therein coupled to said secondary outlet port of said secondary fluid reservoir chamber through a secondary fluid outlet conduit to selectively receive fluid from said secondary fluid reservoir chamber.

17. The pressure controlled valve apparatus of claim 15 wherein said fluid collector container includes a fluid outlet formed on the lower portion thereof and a valve disposed in operative relationship relative to said fluid outlet to selectively empty said primary fluid chamber.

18. The pressure controlled valve apparatus of claim 3 further including a filter disposed within said primary fluid reservoir chamber to filter fluid fed through said centrally disposed fluid outlet channel of said primary fluid reservoir chamber.

19. The pressure controlled valve apparatus of claim 1 further including an air priming means comprising a sealing mmember having a recess formed on the surface thereof rotatably mounted on said fluid reservoir, at least one air inlet aperture and an air outlet aperture formed in the upper portion of said fluid reservoir and anair outlet conduit in open fluid communication with said air outlet aperture such that when said sealing member is rotated to align said flow recess relative to said air inlet aperture and said air outlet aperture air is fed from said fluid fluid reservoir through said air outlet conduit.

20. A pressure controlled valve apparatus for use with a catheter to selectively control fluid flow therefrom comprising a fluid reservoir including a primary fluid reservoir chamber and a secondary fluid reservoir chamber in open fluid communication relative to each other to receive fluid from the catheter and a fluid flow control including a primary control valve and a secondary control valve each selectively movable between a frrst and second position, the primary control valve disposed to seal said primary fluid reservoir chamber when in said first position and to unseal said primary fluid reservoir chamber when in said second position in response to first predetermined pressure to release fluid from the catheter and said primary fluid reservoir chamber to a fluid collection container and said secondary control valve disposed to seal said secondary fluid reservoir chamber when in said first position and to unseal said secondary fluid reservoir chamber when in said second position in response to a second predetermined pressure to release fluid from the catheter and said secondary fluid reservoir chamber to said fluid collection container, said primary and secondary control valves each comprising an outer valve element and a concentric inner valve element cooperatively forming a fluid flow feed channel between then such that fluid flow through said primary control valve holds the inner valve element in said second position by capillary force created by fluid flow through fluid flow feed channel and thereafter when flow from primary valves ceases to occur.

21. The pressure control valve apparatus of claim 20 wherein said primary and secondary control valves each comprises an outer hollow valve element including a lower valve bias seat formed therein and an inner hollow valve element including an upper valve bias seat formed therein disposed in spaced relationship relative to said outer hollow valve element to cooperatively form a fluid flow feed channel therebetween, said inner hollow valve element movable between a first and second position and a bias means operative disposed in said lower valve bias seat and said upper valve bias seat to normally maintin said inner hollow valve element in said first position.

22. The pressure control valve apparatus of claim 21 wherein said primary and secondary outlets each comprises a valve seat disposed in operative relationship to an aperture formed in the lower portion of said corresponding fluid reservoir chamber.

23. The pressure control valve apparatus of claim 22 wherein each said valve seat comprises an upper reduced portion at least partially disposed within said corresponding aperture and a lower enlarged portion having a centrally disposed fluid outlet channel in open fluid communication with the interior of said corresponding fluid reservoir chamber.

24. The pressure control valve apparatus of claim 23 wherein each said outer hollow valve element comprises an upper enlarged member affixed to said lower enlarged portion of said corresponding valve seat and a lower reduced portion including a outlet port formed therethrough having said corresponding lower valve bias seat formed therein.

25. The pressure control valve apparatus of claim 24 wherein each said inner hollow valve element comprises an upper reduced member including a seal formed on the upper portion thereto and said corresponding upper valve bias seat formed on the inner portion thereof and a lower enaarged member having at least one fluid flow aperture formed on the lower portion thereof.

26. The pressure control valve apparatus of claim 25 wherein each said seal comprises a reduced intermediate portion and upper alignment portion to cooperatively retain a seal element thereon, said corresponding valve bias being retained by said corresponding upper and lower bias seats normally biasing each said inner hollow valve element in said first position such that each said corresponding seal element seals each said corresponding centrally disposed fluid outlet channels.

27. The pressure controlled valve apparatus of claim 26 further comprises a fluid collector container including a primary fluid chamber having a primary inlet formed therein coupled to said primary outlet port of said primary fluid reservoir chamber through a primary fluid outlet conduit to selectively receive fluid from said primary fluid reservoir chamber and a visual monitor compartment having a secondary inlet port formed therein coupled to said secondary outlet port of said secondary fluid reservoir chamber through a secondary fluid outlet conduit to selectively receive fluid from said secondary fluid reservoir chamber.

28. The pressure controlled valve apparatus of claim 27 wherein said fluid collector container includes a fluid outlet formed on the lower portion thereof and a valve disposed in operative relationship relative to said fluid outlet to selectively empty said primary fluid chamber.

29. The pressure controlled valve apparatus of claim 20 further including a filter disposed within said primary fluid reservoir chamber to filter fluid fed through said centrally disposed fluid outlet channel of said primary fluid reservoir chamber.

30. The pressure controlled valve apparatus of claim 20 further including an air priming means comprising a sealing member having a recess formed on the surface thereof rotatably mounted on said fluid reservoir, at least one air inlet aperture and an air outlet aperture formed in the upper portion of said fluid reservoir and an air outlet conduit in open fluid communication with said air outlet aperture such that when said sealing member is rotated to align said flow recess relative to said air inlet aperture and said air outlet aperture air is fed from said fluid reservoir through said air outlet conduit.

* * * * *